United States Patent [19]

Nickolls et al.

[11] Patent Number: 5,251,626
[45] Date of Patent: Oct. 12, 1993

[54] APPARATUS AND METHOD FOR THE DETECTION AND TREATMENT OF ARRHYTHMIAS USING A NEURAL NETWORK

[75] Inventors: Peter Nickolls, Vaucluse; Geoff Drane, Annandale; Barry Flower, Manly; Paul Lunsmann, Birchgrove; Robert Dodd, Gladesville; David Bassin, Coogee; John Wickham, Fivedock; Tony Murphy, Homestead West, all of Australia

[73] Assignee: Telectronics Pacing Systems, Inc., Engelwood, Colo.

[21] Appl. No.: 918,934

[22] Filed: Jul. 22, 1992

Related U.S. Application Data

[60] Division of Ser. No. 759,603, Sep. 13, 1991, abandoned, which is a continuation of Ser. No. 547,958, Jul. 3, 1990, abandoned.

[51] Int. Cl.$^5$ .............................................. A61N 1/365
[52] U.S. Cl. ........................................................ 607/14
[58] Field of Search ...................... 128/419 D, 419 PG

[56] References Cited

U.S. PATENT DOCUMENTS

| | | | |
|---|---|---|---|
| 3,857,398 | 12/1974 | Rubin | 128/419 D |
| 3,950,733 | 4/1976 | Cooper et al. | 307/201 |
| 4,202,340 | 5/1980 | Langer et al. | 128/419 D |
| 4,303,075 | 12/1981 | Heilman et al. | 128/419 D |
| 4,375,817 | 3/1983 | Engle et al. | 128/419 D |
| 4,407,288 | 10/1983 | Langer et al. | 128/419 D |
| 4,440,172 | 4/1984 | Langer | 128/419 D |
| 4,473,078 | 9/1984 | Angel | 128/419 D |
| 4,693,253 | 9/1987 | Adams | 128/419 D |
| 4,702,253 | 10/1987 | Nappholz et al. | 128/419 PG |
| 4,712,555 | 12/1987 | Thornander et al. | 128/419 PG |
| 4,742,458 | 5/1988 | Nathans et al. | 364/413.06 |
| 4,827,936 | 5/1989 | Ploss et al. | 128/419 D |
| 4,869,252 | 9/1989 | Gilli | 128/419 D |
| 4,873,455 | 10/1989 | Chambost et al. | 307/201 |
| 4,895,151 | 1/1990 | Grevis et al. | 128/419 PG |
| 4,905,697 | 3/1990 | Heggs et al. | 128/419 PG |
| 4,940,054 | 7/1990 | Grevis et al. | 128/419 PG |
| 4,949,719 | 8/1990 | Ploss et al. | 128/419 D |
| 4,967,749 | 11/1990 | Cohen | 128/419 PG |
| 5,092,343 | 3/1992 | Spitzer et al. | 128/702 |

OTHER PUBLICATIONS

Robert Hecht-Nielsen, "Neurocomputing: Picking the Human Brain", IEEE Spectrum, Mar. 1988, pp. 36-41.

Primary Examiner—William E. Kamm
Attorney, Agent, or Firm—Gottlieb, Rackman & Reisman

[57] ABSTRACT

An apparatus and method for the detection and treatment of arrhythmias using a processor having a neural network with a hierarchical arrangement including a first lower level for classifying individual waveforms, a second higher level for diagnosing detected arrhythmias and a third higher level for the application of therapy in response to a diagnosed arrhythmia. The neural network may be a back propogation neural network or an associative memory type neural network. The arrhythmias detected may be at least one of bradycardia, tachycardia and fibrillation. The apparatus may include a cardioverting/defibrillating pacemaker. In general, the apparatus acquires physiological signals representative of heart activity in a patient. A neural network receives the physiological signals and determines if any arrhythmia is present, and if present, selects therapy to be applied to the heart. A therapy generator then applies the therapy selected by the neural network. The physiological signals may be processed or unprocessed ECG signal, signals indicative of the properties of the blood including the presence of gases, blood temperature, and blood flow signals or signals representative of ventricular wall impedance or ventricular volume.

10 Claims, 9 Drawing Sheets

APPARATUS AND METHOD FOR THE DETECTION AND TREATMENT OF ARRHYTHMIAS USING A NEURAL NETWORK

This is a division of application Ser. No. 759,603, filed Sep. 13, 1991, now abandoned, which was a continuation of application Ser. No. 547,958, filed Jul. 3, 1990, now abandoned.

TECHNICAL FIELD

This invention relates to medical devices which monitor the cardiac state of a patient by sensing the patient's intrinsic rhythm for the presence of arrhythmias and which deliver therapy in the form of electrical energy to cardiac tissue in an attempt to revert ventricular fibrillation (VF) and other detected arrhythmias and restore a normal sinus rhythm to the patient.

The invention describes an apparatus and method for the detection and treatment of cardiac arrhythmias by the use of a neural network. The invention utilizes a neural network for arrhythmia recognition, diagnosis, and therapy control or a warning system to a patient. The neural network used in the invention is a parallel processing system having the capability of recognizing VF's and other forms of arrhythmias in real time with a greatly improved accuracy and lower power consumption than is possible with present arrhythmia control systems. The invention provides a device with an enhanced complex therapy control further having the ability to make diagnostic decisions using incomplete data, and has an application to all types of heart pacemaker sensing and therapy including bradycardia and rate responsive pacing.

As used herein the term arrhythmia refers to any abnormal rhythm of the heart which may be amenable to treatment by electrical discharges, and specifically includes tachyarrhythmias, fibrillation, tachycardias, supraventricular tachycardias (SVT), ventricular tachycardias (VT), ventricular flutter ventricular fibrillation (VF), and bradycardia.

BACKGROUND OF THE INVENTION

VF is a potentially life threatening cardiac tachyarrhythmia producing an immediate loss of blood pressure. In a normally functioning heart, the muscle fibers are stimulated by a wave-like electrical excitation originating in the sino-atrial node in the right atrium. The excitation then proceeds to the atrium and then to the ventricles of the heart. This wave-like excitation then triggers the ventricular muscle fibers by producing a sequential depolarization of adjacent cells, thereby effecting an efficient contracting and pumping action which is the normal mechanical activity of the heart. In certain individuals and under certain conditions, the organized wave-like pattern of electrical excitation becomes interrupted and VF results, this being a disorganized, random contraction and relaxation of the fibers of the ventricle. During VF, the muscle fibers are electrically depolarizing and repolarizing in a random manner thereby resulting in a chaotic twitching of the ventricular muscle with no effective pumping of blood being accomplished. This inevitably results in loss of consciousness of the patient and a high probability of death if appropriate therapy is not given to the patient.

By the application of a sufficient discharge of electric current to the ventricular muscle fibers, it is possible to depolarize an adequate number of the fibers at the one time to re-establish synchrony within the heart thereby enabling the ventricles to resume their normal rhythmic pumping activity.

VF must be treated within a short period of time following onset or the patient may die. A widely used treatment of VF's today is the delivery of a sufficiently powerful external electric shock to the ventricles of the heart. At present, there is an identifiable population of patients who survive an episode of VF due to prompt therapy. Although these patients may survive their first episode of VF due to the efforts of responsive hospital attendants, their long term chances of survival are not high. It is well known that within minutes of the onset of VF, irreversible changes begin to occur in the brain and other vital organs. It is therefore desirable to effect defibrillation as quickly as possible. For these patients who are becoming increasingly more identifiable, an alternative treatment now becoming more and more widely used is the implantable automatic defibrillator device which combines defibrillation and both bradycardia and antitachycardia pacing in a single device.

Prior to defibrillators, there existed devices for applying pacing pulses to the heart known as pacemakers. These were initially developed to electrically stimulate hearts that were unable to beat at a rate sufficient to maintain a life sustaining cardiac output. The first devices delivered electrical stimuli at a fixed rate regardless of the heart's function or the body's physiological needs.

At a later time devices were developed that stimulated the heart only if it failed to beat above a predetermined rate. Such devices sensed the electrical activity of the heart, usually in the right ventricle. Later developments saw the introduction of pacemakers that sensed and stimulated in both the right atrium and ventricle.

Additionally, pacemakers were introduced in order to obtain a measure of the body's physiological needs and which responded by altering the paced rate to meet the demand, for example, by sensing the respiratory rate and then increasing the heart rate as the respiratory rate increased. Such a pacemaker is disclosed in U.S. Pat. No. 4,702,253 to Nappholz et al. In this device, electrodes are placed in a blood vessel in the vicinity of the patient's pleural cavity, a known current field is established in the blood, and the blood impedance in the field is measured. The impedance is a function of the pleural pressure which, in turn, is a function of the patient's minute volume.

A major step in the pacemaker field saw the development of devices that electrically sensed the presence of a ventricular tachyarrhythmia and delivered a defibrillating D.C. shock to revert the heart to a normal rhythm. More advanced devices were developed that attempted to pace hearts undergoing a supra-ventricular or ventricular tachyarrhythmia back into a normal rhythm. This technique is known as antitachycardia pacing (ATP).

A further step included the development of automatic cardiac defibrillator devices which sense and analyze the electrical activity of the heart. Such a device is described in U.S. Pat. No. 3,857,398. The electrical activity of the heart has typically been detected by a pair of electrodes placed in or around the heart. This method enables detection of an ECG showing a record of R and T waveforms indicating stages of electrical depolarization and repolarization of the ventricles of the heart.

Combined devices have been developed that can act both as pacemakers and as arrhythmia control systems. These devices are able to pace a heart that is beating too slowly, to cardiovert/defibrillate a heart and to pace a heart undergoing a ventricular tachyarrhythmia, back into a normal rhythm.

An example of such a combined implantable device is described in U.S. Pat. No. 4,940,054, of Richard Grevis and Norma L. Gilli entitled "Apparatus and Method for Controlling Multiple Sensitivities in Arrhythmia Control Systems Including Post-therapy Pacing Delay".

The above mentioned device is a microcomputer based arrhythmia control system. The device is able to be programmed to many different bradycardia pacing modes. It uses a telemetric link to communicate with the physician. Variables such as the bradycardia support pacing rate and the atrio-ventricular (AV) delay can be programmed to suit the needs of the recipient of the device. However, such parameters can only be altered by a telemetric link. There is no provision for the device to adjust its programmed parameters in a learning response mode.

The use of a telemetric link allows not only the reprogramming of a device, but also the interrogation of a device by a clinician. Some devices are also fitted with vibrating warning devices to indicate to the patient certain error states within the device and/or malfunctions of the heart. The idea is to hasten the patient's presentation to the clinician to allow interrogation of the device.

It was found that existing devices which relied solely on electrical sensing in order to determine the state of the cardiac function still had some inherent limitations. For example, these devices have at times been confused by the presence of electrical noise in their sensing circuits thereby resulting in difficulty in distinguishing a VF. Even when the ECG classification is correct, the heart may not be pumping sufficient blood. It was found to be more effective by adding to the sensing capabilities certain manipulations of the right ventricular pressure signal as described in the co-pending patent application of Kenneth A. Collins, Ser. No. 481,364, filed Feb. 16, 1990, now U.S. Pat. No. 5,083,563, entitled "An Implantable Automatic and Haemodynamically Responsive Cardioverting/Defibrillating Pacemaker" which relates to a device that adds the ability to transduce haemodynamic compromise to a cardioverting-/defibrillating pacemaker. It includes the provision of switching to the best mode of pacing for a given cardiac state by sensing the right ventricular filtered peak-to-peak amplitude (RVFPPA) or the right ventricular pulse pressure function (RVPPF), as well as the electrical activity of the right ventricle.

There still remain many shortcomings in existing devices. Of particular note is their lack of speed and accuracy in the detection of complex arrhythmias as well as in the diagnosis and the application of appropriate therapy. The recipients of existing cardioverter/-defibrillators and cardioverting/defibrillating pacemakers may still face the risk of the inappropriate delivery of defibrillation therapy. Such therapy is not without risk of damage to the myocardium. Furthermore, unwarranted discharge of the device causes pain to the conscious patient, instilling great anxiety, as well as shortening the life of the device's batteries. Besides the risk of false positives, there is also the risk of false negatives when a needed therapy fails to be delivered. This can be a life threatening situation to a patient.

A further problem with existing defibrillator devices is that their use is resisted by some cardiologists who prefer the use of toxic beta-blockers, such as amioderone, despite the fact that the arrhythmia may still not be under control, as a preference to an implantable defibrillator device which has a large delay between the detection of a tachyarrhythmia and the application of therapy to a patient. A large delay results in the patient losing consciousness, thereby having a profound effect on his ability to continue driving a motor vehicle. This situation could therefore be extremely hazardous to the driver's own life as well as the lives of others. Furthermore, the loss of a driver's licence is a very undesirable fate in itself. The reason for such a large delay in existing implantable defibrillator devices is due not only to the diagnostic component but also to the large delay in the charging time of the defibrillator capacitor.

Another problem with present implantable combined pacemaker-defibrillator devices is the high level of power consumption involved. Such devices, which are typically microprocessor controlled, use a continuous high level of power due to the continual "wakened" state of the detection, diagnostic and therapy control phases of the device. A high level of power consumption significantly reduces the life of the battery, which in turn places trauma on the patient due to the need to have an early battery replacement in the implantable device.

SUMMARY OF THE INVENTION

It is an object of the invention to provide a device which is capable of recognizing arrhythmias in real time with far higher accuracy than is possible with existing devices.

It is a further object of the invention to provide a device which is capable of providing a far more complex therapy control than is possible with present pacemaker-defibrillator devices.

It is a further object of the invention to provide a device which has a higher speed during the diagnosis of arrhythmias than is possible in present devices, thereby reducing the delay time prior to providing appropriate therapy to a patient.

It is a further object of the invention to increase the safety of patients, particularly motor vehicle drivers, by means of a fast recognition procedure which minimizes the possibility of loss of consciousness.

It is a further object of the invention to increase patient safety by reducing greatly the possibility of false positive and false negative decisions by the greatly improved accuracy of the diagnostic component of the device of the present invention.

It is an additional object of the invention to provide a device which is able to make decisions based on incomplete data.

It is a further object of the invention to provide an arrhythmia recognition system which is capable of operating at a lower level of power consumption than existing implantable arrhythmia control systems such as combined pacer-defibrillators, thus allowing for longer battery life and thereby safeguarding the patient from the trauma associated with an early battery replacement.

The invention provides an implantable medical device and, more particularly, relates to an apparatus and method for the detection and treatment of cardiac arrhythmias by the use of a neural network. The invention utilizes a neural network for arrhythmia recognition, diagnosis and therapy. The neural network used in the invention is a parallel processing system having the capability of recognizing VF's and other forms of arrhythmias in real time with a greatly improved accuracy and lower power consumption than is possible with present arrhythmia control systems. The invention provides a device with an enhanced complex therapy control further having the ability to make diagnostic decisions using incomplete data.

The invention further provides an arrhythmia control apparatus including a neural network. It includes means for monitoring heart activity in a patient and means for detecting arrhythmias including means for diagnosing detected arrhythmias. The device also includes means for applying appropriate therapy to restore normal sinus rhythm in response to a detected arrhythmia. The means for detecting arrhythmias includes means for sensing physiological signals and means for providing features of the physiological signals as input to the neural network.

The invention further provides an automatic implantable medical device incorporating a neural network. It includes means for monitoring the heart activity in a patient and for detecting arrhythmias including means for sensing physiological signals. It further has the capability of inputting the sensed physiological signals into the neural network. The implantable device also has means for diagnosing detected arrhythmias and for applying appropriate therapy to restore normal sinus rhythm in response to a diagnosed arrhythmia. The means for detecting arrhythmias is controlled by the neural network.

There is further provided an implantable tachyarrhythmia detection apparatus including sensing means for sensing a raw physiological signal in a patient. The apparatus has a neural network along with means for providing the sensed raw physiological signal as input to the neural network for classifying and diagnosing the presence of a tachyarrhythmia. The apparatus also includes a means for warning the patient of a detected tachyarrhythmia.

There is also provided a method of tachyarrhythmia detection including sensing physiological signals in a patient, providing the sensed physiological signals as input to a neural network, and operating the neural network for the classifying and diagnosing of the presence of a tachyarrhythmia.

In one embodiment of the invention the neural network is a back propagation neural network. The neural network operates in a manually trained mode with the option of being placed into a self-learning mode. Furthermore, the network provides a hierarchical arrangement containing at least three hierarchical levels. A first lower level is used for classifying individual waveforms. A second higher level is used for diagnosing detected arrhythmias, and a third higher level operates for therapy application to a diagnosed arrhythmia. Preferably the arrhythmia control apparatus is a cardioverting-/defibrillating pacemaker, although it may have application in a cardioverter/defibrillator alone. It has application to bradycardia pacing and rate responsive pacemakers either alone or when used in combination with cardioverting/defibrillating pacemakers. The invention has application in detecting and reverting tachyarrhythmias such as VT, SVT, VF and other forms of fibrillation such as atrial fibrillation. It applies to both single and dual chamber devices. When a system for warning a patient is included, it may be by means of light, sound, electrical stimulation, or other well known methods familiar to those skilled in the art. The invention preferably applies to implantable devices, but also may be used externally. It is preferable that the device is programmable and operates by means of telemetry. The physiological signals detected by the device may be raw ECG signals, blood impedance measurement waveforms, VFPPA or VPPF signals, arterial pO2, pCO2, pH, blood temperature, ventricular wall impedance, ventricular volume (measured by blood impedance), and blood flow (measured by ultrasonic transducer) signals, or other similar signals known to those skilled in the art. These physiological signals may be used by the device either alone or in combination.

In another embodiment of the invention, the neural network is an associative memory of the type known as a Hopfield network, using three hierarchical networks as in the previous embodiment.

SUMMARY OF TERMS

Neural Networks . . . Analog, digital, or a hybrid combination of analog and digital processor arrays with an architecture that has features similar to the type of architecture found in animal brains. They have advantages over conventional digital processors in being faster, drawing a lower amount of power in the case of analog or hybrid arrays, and having a lower susceptibility to errors. Neural networks possess the property of redundancy resulting in any individual power failures leading to a gradual, rather than a catastrophic reduction in performance. Neural networks are known for their use in pattern recognition tasks. When used as such, and there is some "fuzziness" in the incoming information (for example, missing or widely varying data), neural networks have a lower error rate than conventional pattern recognition systems.

In the past, neural networks have been associated with such applications as visual pattern recognition, motion detection, adaptive pattern recognition, and other applications. The present invention identifies a new use for neural networks in the complex biomedical field of implantable devices for arrhythmia detection, diagnosis and therapy. The inventors have found that by modifying and adapting a neural network to the field of arrhythmia control, a number of significant advantages have been identified, with particular emphasis on the speed, accuracy, and low power consumption of implantable arrhythmia control devices.

In one embodiment of the invention a back propagation model neural network has been modified. It operates by taking in the raw ECG signal or features extracted from the raw signal. The neural network is manually trained. In another embodiment of the invention, the network is put into a self-learning mode.

In one embodiment of the invention, the network has been arranged into a hierarchical fashion with the lower levels classifying the individual ECG waveforms, and with a higher level of the network being used to form a diagnosis. In another embodiment the network uses a still higher level for treatment or therapy. Preferably, other signals besides ECG signals can be input into the network. Additionally, in order to conserve power, it has been found preferable to power only the lowest level of the network, with the upper levels being powered as required. With the introduction of an acceptable delay into the system, the whole network may be in a "sleep state" until aroused by a simple QRS event detector. Arousal may be determined for every event or only when the event rate falls outside a preset window.

Arrhythmia . . . Any abnormal rhythm of the heart which may be amenable to treatment by electrical discharges, and specifically includes tachyarrhythmias, fibrillation, tachycardias, supraventricular tachycardias (SVT), ventricular tachycardias (VT), ventricular flutter and ventricular fibrillation (VF), and bradycardia.

Therapy . . . The processes used between the detection and reversion of an arrhythmia and includes the actions of antitachycardia or bradycardia pacing and cardioversion.

Cardioversion . . . The discharge of electrical energy into the cardiac tissue in an attempt to terminate or revert a tachycardia and may range from a high (40 Joules or more) to a low (less than 1 Joule) energy discharge. The discharge may be monophasic or biphasic, but is not restricted to these waveforms. Cardioversion shocks may or may not be synchronized to the rhythm of the heart.

Defibrillation . . . A particular example of cardioversion, usually including high energy unsynchronized shocks.

ECG . . . Electrocardiograph. The ECG is strictly speaking the graphical representation of the electrical activity of the heart. However the term ECG is used loosely to refer to the electrical activity of the heart. The electrical activity of the heart can be sensed on the surface of the skin, on the heart or in the heart.

VF . . . Ventricular fibrillation

VT . . . Ventricular tachycardia

SVT . . . Supraventricular tachycardia

Pacemaker . . . A device capable of electrically stimulating the heart to contract. Most such devices can also sense the electrical activity of a contracting heart and react to alterations in its electrical function. Most such devices are implanted and, if programmable, are interacted via a telemetric link.

Rate responsive (or physiological) pacemakers . . . Pacemaking devices that are able to sense and respond to some indicator of increased tissue oxygen demand, such as, for example, respiratory rate. They respond by altering the paced heart rate to meet the changes in oxygen requirements.

Cardioverter/defibrillator . . . A device that can sense the presence of tachyarrhythmias and deliver an electric shock to a heart in order to revert it back to a normal rhythm. The difference between a cardioverter and a defibrillator lies only in the amount of energy delivered to the heart. Cardioversion is usually used to refer to low energy shocks and defibrillation to high energy shocks. A cardioverter/defibrillator is usually capable of supplying energies in a range of less than 1 joule to more than 40 joules. These shocks may or may not be synchronized with the R wave of the ECG.

Cardioverting/defibrillating pacemaker . . . A device that can perform both cardioverting/defibrillating and pacemaking functions. When referred to herein it applies to devices that deliver their energy synchronously with a detected R-wave as well as to devices that do not. When used the term will usually apply to devices that electrically sense/stimulate via electrodes in the right ventricle and atrium but the term may also apply to devices that do so only in the right ventricle, in the right atrium alone, in multiple heart chambers, via epicardial patches or leads, or via other sense/stimulation configurations.

Antitachycardia pacing (ATP) . . . A technique implemented in some pacemaking devices to pace a rapidly and abnormally beating heart back into a more normal rhythm. Its use implies that the tachyarrhythmia detected is considered not to be so sufficiently haemodynamically compromising that it will endanger vital organs within the anticipated treatment time. ATP may produce a more malignant tachyarrhythmia; for example ventricular tachycardia (VT) may be paced into ventricular fibrillation (VF). For this reason ATP is normally implemented only when there is the option to use cardioversion/ defibrillation therapy.

VFPPA . . . The filtered peak-to-peak amplitude of the ventricular pressure waveform is obtained after filtering out, with a highpass filter, any voltage offset to the pressure waveform, and is therefore a measure of the difference between the systolic and diastolic pressures in the ventricle.

VPPF . . . The ventricular peak pressure function is the integral of the filtered and rectified VP waveform. It is a measure of the work performed by the heart in producing the increase in pressure occurring with each heart contraction.

BRIEF DESCRIPTION OF THE DRAWINGS

Further objects, features and advantages of the invention will become apparent upon consideration of the following detailed description in conjunction with the drawings, in which.

BEST MODE OF THE INVENTION

Figure 1:
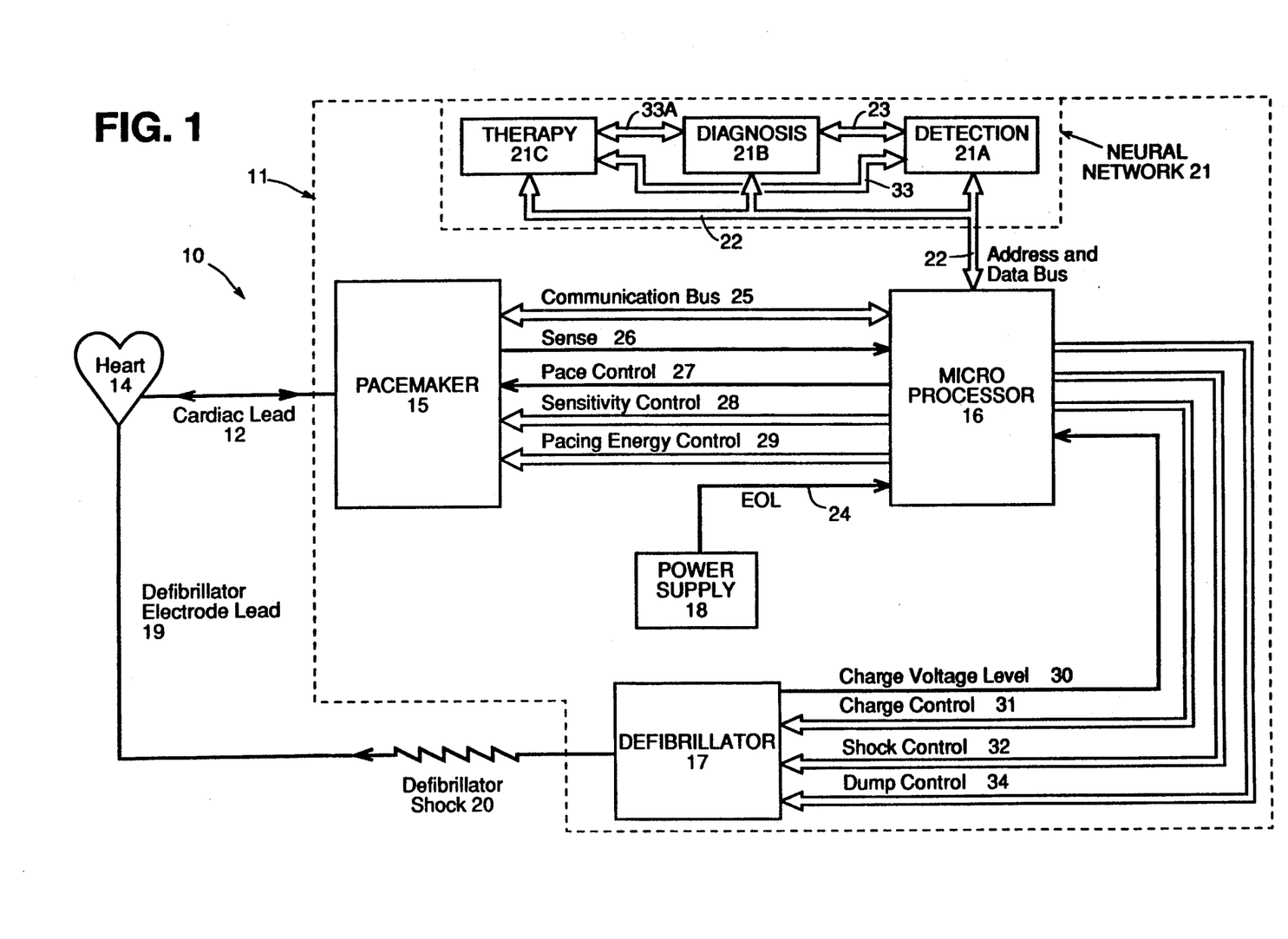
FIG. 1 is a block diagram of an arrhythmia control system (ACS)

FIG. 1 is a block diagram of an arrhythmia control system 10. System 10 is designed to be implantable and includes a pulse module 11 and appropriate leads. More particularly, system 10 will generally include a cardiac lead extending to the atrium of a patient's heart for the administration of therapy to the atrium or a cardiac lead 12 extending to the ventricle of a patient's heart 14 for the administration of therapy to the ventricle. System 10 generally also includes a pacemaker 15 for the detection of analog signals representing cardiac electrical activity and for the delivery of pacing pulses to the heart; a neural network 21 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, neural network 21 and defibrillator 17 by suitable electrical conductors (not shown). Defibrillator 17 produces a high voltage to charge its capacitors and then discharges them in response to control signals from neural network 21. A defibrillator electrode lead 19 transfers the energy of a defibrillator shock 20 from the implanted pulse module to the surface of the heart 14.

A microprocessor 16 is connected to a neural network 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control bus 29. As also more fully described below, microprocessor 16 is connected to defibrillator 17 by a charge level line 30, a charge control bus 31, a shock control bus 32, and a dump control bus 34.

Neural network 21, as more fully described below, is a back propagation neural network operating with three hierarchical levels 21A, 21B, and 21C. Level 21A is used for detection. Level 21B is used for diagnosis, and level 21C is used for therapy control. All three levels are connected to the microprocessor 16 by address and data bus 22. Level 21A is connected to level 21B by address and data bus 23, and to level 21C by address and data bus 33. Level 21B connects to level 21C by means of address and data bus 33A.

Figure 2:
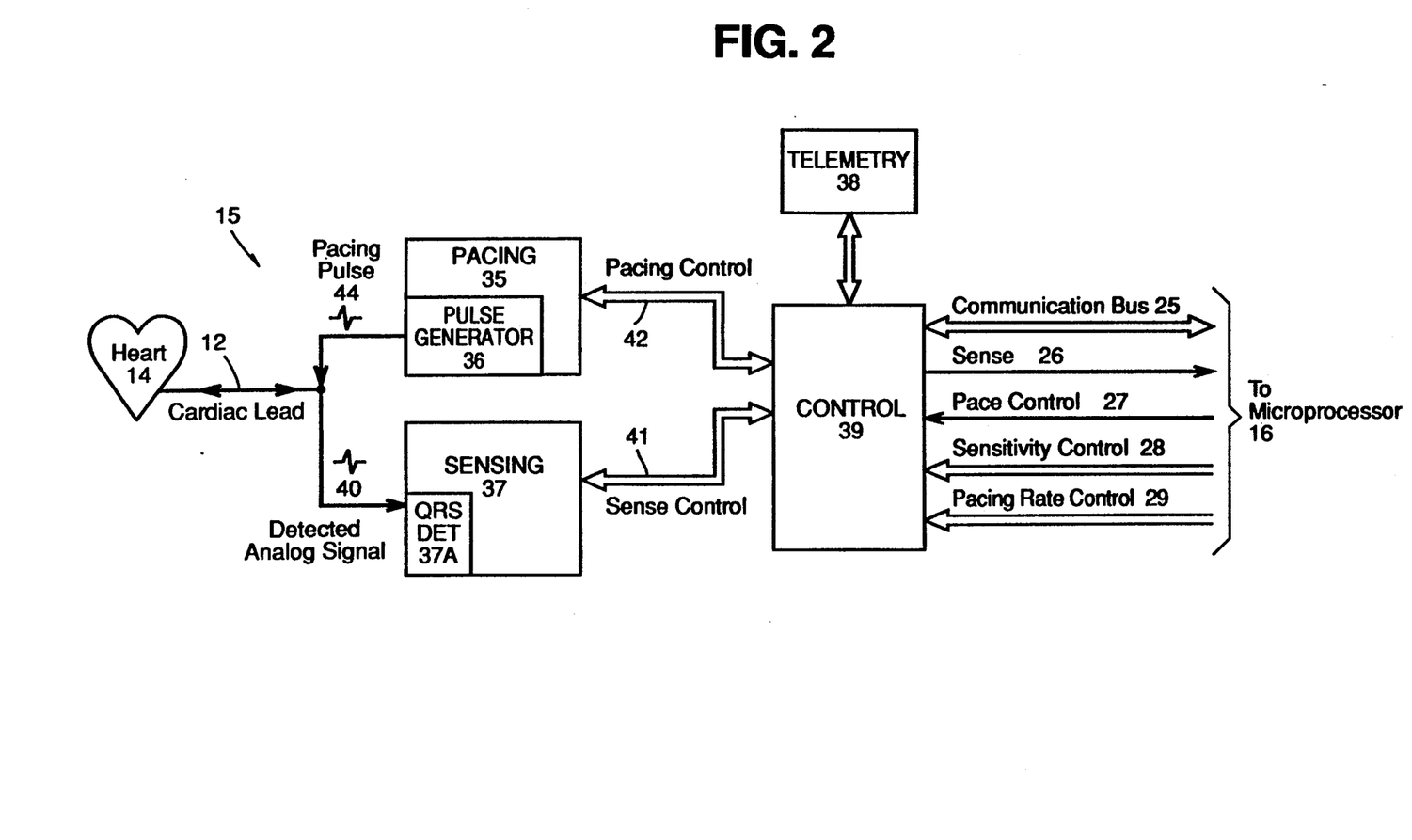
FIG. 2 is a block diagram of the pacemaker of FIG. 1.

Referring to FIG. 2, pacemaker 15 comprises pacing circuit 35 which includes a pacing pulse generator 36, sensing circuit 37, and telemetry circuit 38. In addition, there is a control block 39 which includes an interface to microprocessor 16.

In operation, sensing circuit 37 detects analog signals 40 from the heart 14 in an internal QRS detector 37A and converts the detected signals to digital signals. Furthermore, sensing circuit 37 receives an input sense control signal (which determines the sensitivity of the detection circuits in sensing circuit 37) by way of a sense control bus 41 from control block 39. As more fully described below, a change in this sensitivity will affect the voltage deviation required at the sensing electrode for a sense to be registered.

Pacing circuit 35 also receives inputs from control block 39 including a pace control and a pacing energy control by way of pacing control bus 42 which carries the signals on pace control line 27 and pacing energy control bus 29. The pace control determines the type of pacing to occur The magnitude of the pulse energy is determined by the pacing energy control. Pacing circuit 35 causes pulse generator 36 to generate the pacing pulse 44 which is delivered to the patient's heart 14 by means of cardiac lead 12.

Telemetry circuit 38 provides a bi-directional link between control block 39 of pacemaker 15 and an external device such as a programmer. It allows data such as the operating parameters to be read from or altered in the implanted pulse module 11.

Figure 3:
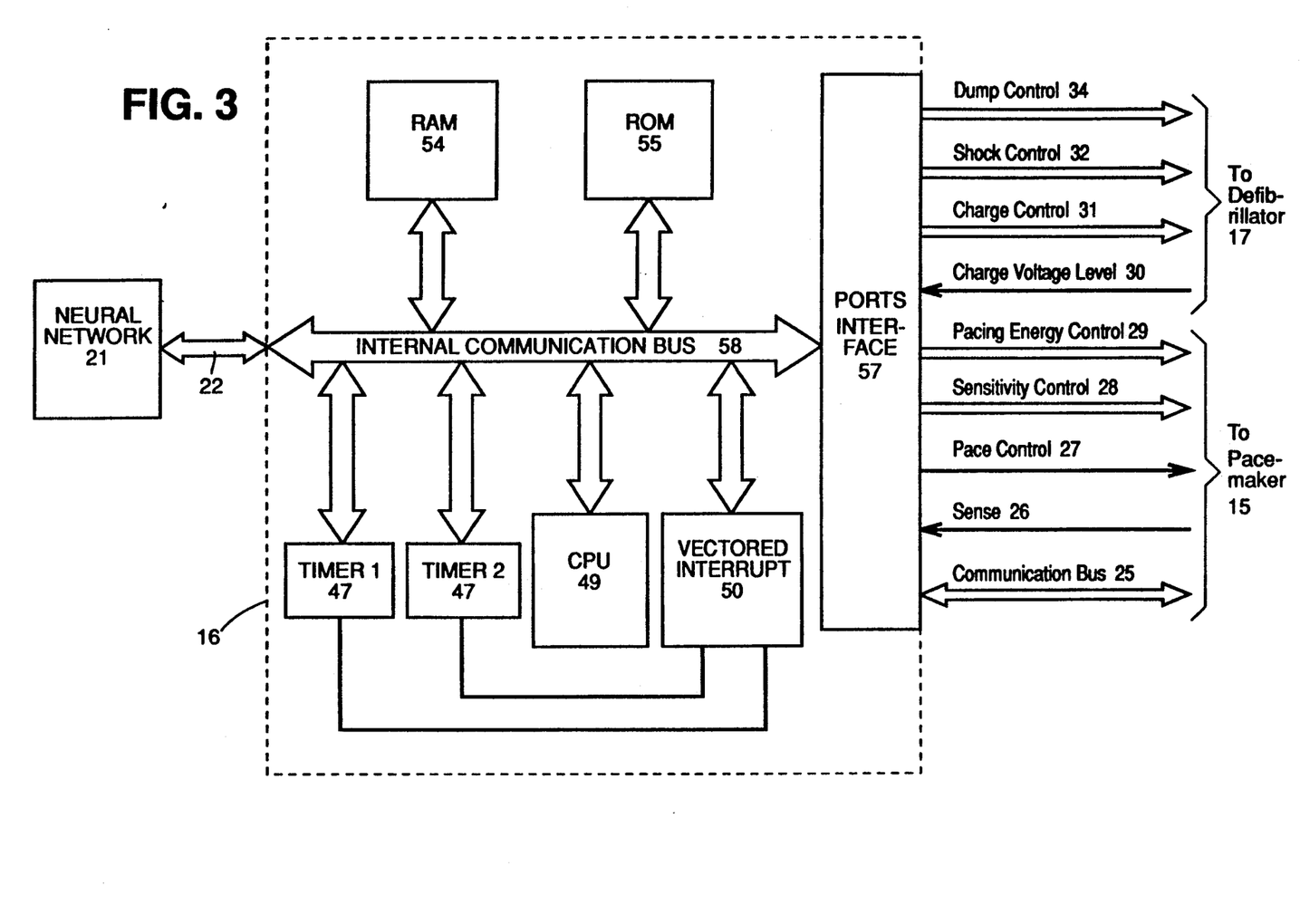
FIG. 3 is a block diagram of the microprocessor of FIG. 1.

Referring to FIG. 3, microprocessor 16 comprises two 16-bit timers 47 and 48, CPU 49, vectored interrupt block 50, RAM 54, ROM 55, ports interface 57 and an internal communications bus 58. RAM 54 acts as a scratch pad and active memory during execution of the various programs stored in ROM 55 and used by microprocessor 16. These programs include system supervisory programs, detection algorithms for detecting various arrhythmias, and programming implementing the logic flow diagram of FIG. 4, as well as storage programs for storing, in external memory 21, data concerning the functioning of module 11 and the electrogram provided by cardiac lead 12. Timers 47 and 48 and associated control software implement some timing functions required by microprocessor 16 without resort entirely to software, thus reducing computational loads on and power dissipation by CPU 49.

Signals received from telemetry circuit 38 permit an external programmer (not shown) to change the operating parameters of pacemaker 15 by supplying appropriate signals to control block 39 via telemetry circuit 38. Communication bus 25 serves to provide signals indicative of such control to microprocessor 16. Thus, it is also possible for an external programmer to control operation of defibrillator 17 by means of signals provided to microprocessor 16.

Appropriate telemetry commands may cause telemetry circuit 38 to transmit data to the external programmer. Data stored is read out, by microprocessor 16, on to communications bus 25, through control block 39 in pacemaker 15, and into telemetry circuit 38 for transmission to the external programmer by a transmitter in telemetry circuit 38.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place.

Other pacemaker control outputs generated by microprocessor 16 include a pacing energy control signal on pacing energy control bus 29 which determines the magnitude of the pulse energy, and a sensitivity control signal on sensitivity control bus 28, which determines the sensitivity setting of the sensing circuit.

Microprocessor 16 provides to defibrillator 17 a shock control signal on shock control bus 32 which indicates that a shock is to be delivered to the patient, a dump control signal on dump control bus 34 which indicates that a shock is to be dumped at an internal load within defibrillator 17, and a charge control signal on charge control bus 31 which determines the voltage level of the shock to be delivered. Charge voltage level line 30 provides a digital signal representative of charge voltage from an analog to digital converter within defibrillator 17, thus providing a feedback loop which assures that a shock of proper energy level is delivered by defibrillator 17.

Figure 3A:
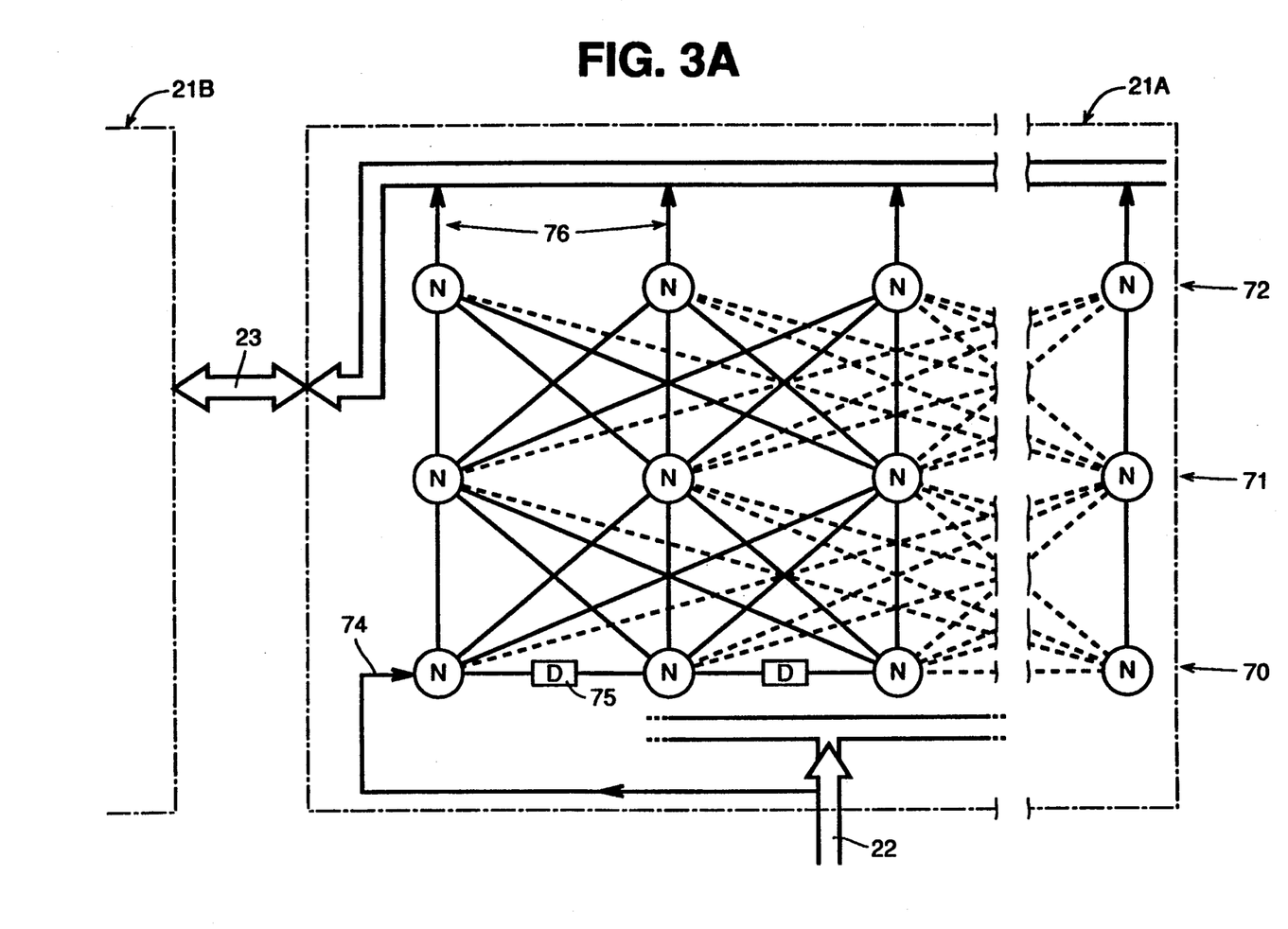
FIG. 3A is a block diagram of a portion of the neural network of FIG. 1.

FIG. 3A is diagram of a portion of the neural network 21 shown in FIG. 1, with particular reference to the detection hierarchical level 21A. As shown, an ECG signal on line 74 of address and data bus 22 is fed into the input nodes N in layer 70 of the neural network 21A in a serial fashion with delay elements D, one of which is further identified at 75, situated between adjacent input nodes. The ECG signal 74 may be in the form of a digital or analog signal and may be fed either as shown via the address and data bus 22 through the microprocessor 16, or directly by means of the cardiac lead 12.

The nodes N in layers 70, 71, 72 may be connected either as an associative memory or as a multi-layer perceptron. The back propagation method is preferably used to train the multi-layer perceptron. The number of input nodes N in layer 70 and hidden layer neurodes N in layer 71 are variable, and may be altered depending upon the selectivity and sensitivity required, and balanced against the allowable complexity. The number of output nodes N in layer 72 is directly related to the number of ECG features 76 in the case of the detection network 21A or classifications in the case of the classification network 21B for which the neural network is trained. Some of the outputs 76 may be fed back to the input nodes N in layer 70. Similarly, feedback may be used in the other two neural networks 21B and 21C.

An alternative formulation of the neural network includes an arrangement whereby the input nodes form a neuron ring either with or without the other layers, so that the ECG signal enters the neural network at one point on the neuron ring.

The neural networks 21A, 21B, and 21C in this embodiment are arranged in a hierarchical fashion so that the output of the first neural network 21A consists of a series of features 76 extracted from the serial input ECG signal 74. These extracted features may include the period between ECG complexes, Q, R, and S wave amplitudes, PR interval, ST interval, ST segment amplitude, P wave duration (width), QRS complex duration, R wave slope, the number of subsidiary R and S waves, R2 and S2 wave amplitude slopes, and the time from the onset of a QRS complex. The extracted features however, are not limited to those mentioned above.

The output of the first neural network 21A is the input to the second neural network 21B. The output of the second neural network 21B is the ECG classification, and becomes the input to the third neural network 21C. The output classification of the second neural network 21B may include normal sinus rhythm, sinus tachycardia, bradycardia, ventricular tachycardia with haemodynamic compromise, ventricular fibrillation, supraventricular tachycardia, atrial fibrillation, nodal re-entry tachycardia, Wolf-Parkinson-White tachycardia, noise, and sympathetic demand. The classifications however, are not limited to those mentioned above. The output of the third neural network 21C becomes the therapy to be delivered to the patient, and returns to the microprocessor 16 via address and data bus 22 which communicates with pacemaker 15 and defibrillator 17 as shown in FIG. 1. Furthermore, the number of output nodes N in the first layer 70 is the same as the number of input nodes N in the second layer 71, and equals the number of features extracted from the ECG signal 74.

A diagram of the second and third hierarchical levels comprising neural networks 21B and 21C has been omitted as these would be identical to neural network 21A, with the exception of the delay elements D of neural network 21A. These elements are absent from neural networks 21B and 21C, as they are required only for the serial ECG input signal, which, as a result of processing in 21A is converted to parallel output signals. In the embodiment described, the three neural networks 21A, 21B, and 21C are each hierarchical levels of the neural network 21.

Other neural network formulations familiar to those skilled in the art include the use of randomly adaptive bidirectional associative memories, temporal associative memories, bidirectional associative memories, and adaptive bidirectional associative memories. However, the type of neural network formulation which may take the place of that described in the present embodiment is not limited to those described above.

Figure 4:
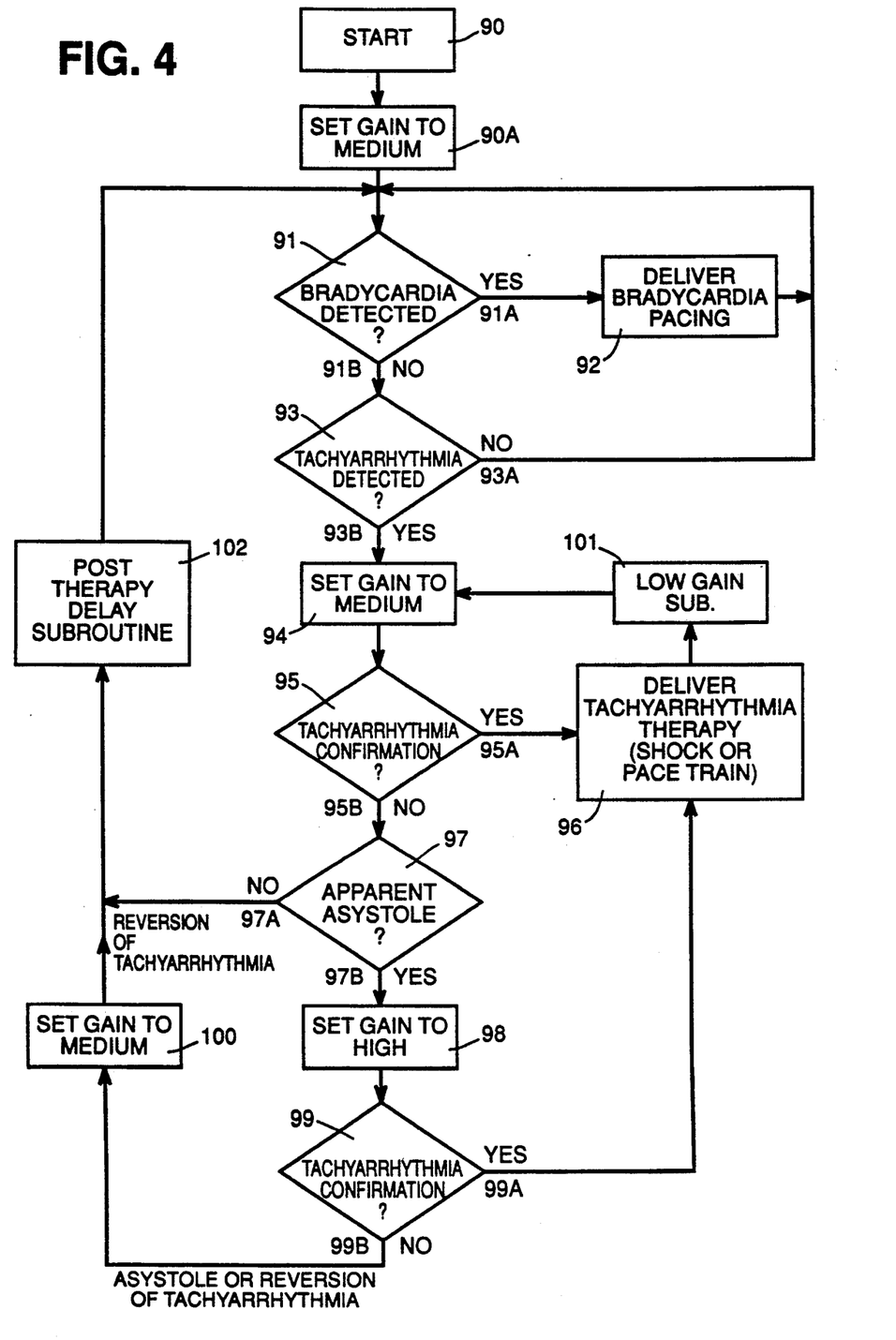
FIG. 4 is a logic flow diagram of the software executed by the neural network of FIG. 3A for multiple sensitivity sensing and post therapy pacing delay in accordance with the invention.

FIG. 4 is a logic diagram of the neural network flow control for controlling the sensitivity of sensing circuit 37 of the device. The neural network 21 has the advantage of operating the flow control with extremely high speed and accuracy. This has particular advantage with the decision making sections of the control logic such as 91 (bradycardia detection), 93 (tachyarrhythmia detection), 97 (apparent asystole), and 99 and 95 (tachyarrhythmia confirmation).

The start of the flow control is shown at 90. At 90A, the sensitivity is set to medium gain. At 91, a determination is made as to whether bradycardia is detected or not. If bradycardia is detected, as shown at 91A, then bradycardia pacing is delivered at 92. This cycle continues until bradycardia ceases to be detected, as shown at 91B. A determination is then made as to whether or not tachyarrhythmia has been detected at 93. If tachyarrhythmia is not detected, as shown at 93A, the program will loop back to 91, and there will be no change or delivering of therapy until the detection of either bradycardia or tachyarrhythmia. If tachyarrhythmia is detected, as shown at 93B, then the sensitivity setting is switched to the medium setting at 94 (if it is not already at that setting).

A decision by the neural network 21 with respect to tachyarrhythmia confirmation then takes place at 95. If a tachyarrhythmia has been confirmed, as shown at 95A, then antitachyarrhythmia therapy is delivered to the patient at 96. This antitachyarrhythmia therapy may take the form of defibrillation shock therapy or a train of antitachycardia pacing pulses.

The time limit for the application of antitachyarrhythmia pacing therapy at 96, prior to the delivery of a shock, is of importance. In this regard, reference is made to U.S. Pat. No. 4,895,151 issued to Richard Grevis and Lorraine Holley, and entitled "Apparatus and Method for Therapy Adjustment in Implantable Cardioverter". In this application, the time limit for application of a shock is determined in accordance with the haemodynamic condition of the patient.

The pacing operation at 96, and more specifically, the manner in which the neural network 21 controls the levels of pacing energy in accordance with events which have occurred, is described in further detail hereinafter with reference to FIG. 10.

On completion of the antitachyarrhythmia therapy, the program executes a low sensitivities subroutine 101, described below with respect to FIG. 5, and then loops back to 94, where sensitivity is set to medium. The program then passes back to 95 for the decision of tachyarrhythmia confirmation.

If there is no confirmation of the tachyarrhythmia at 95, as shown at 95B, then the neural network 21 makes the decision at 97 as to whether the condition of asystole is present in the patient. If there is no asystole, as shown at 97A, then the loop passes back to 91 by way of a post therapy delay subroutine 102 described below with respect to FIG. 6, and the cycle starts again with the decision of bradycardia detection at 91 and the steps which follow from there.

If at 97 there appears to be asystole as shown at 97B, it is of importance to realize that this may be due to the absence of a signal when the sensitivity is at the medium setting. The next step is to confirm whether the condition of asystole is, in fact, present. The reason for this is to differentiate between asystole and a fine VF which would not normally produce a signal in the medium sensitivity setting. To achieve differentiation, switching of the sensitivity to the high setting occurs at 98.

Following the increase in the sensitivity level, the neural network 21 provides a confirmation of tachyarrhythmia at 99. It is at this time that a differentiation between asystole and a tachyarrhythmia occurs. If the condition is a tachyarrhythmia, as shown at 99A, then antitachyarrhythmia therapy is delivered at 96 in the form of defibrillation shock therapy or antitachycardia pacing. The program then loops back to 94 as previously described.

If there is no confirmation of a tachyarrhythmia at 99, as shown at 99B, then there is either the condition of asystole or the tachyarrhythmia has been reverted. At this time, the sensitivity is switched back to the medium setting at 100, and the loop passes back to 91, by way of subroutine 102, for the detection of bradycardia and the cycle as previously described. It is desirable that bradycardia support pacing be inhibited for a programmable period of time after reversion of a tachyarrhythmia to avoid any pro-arrhythmic effect. Such delay may be implemented in one of timers 47 and 48 (FIG. 3) or in software, as in subroutine 102, as described below with respect to FIG. 6.

Figure 5:
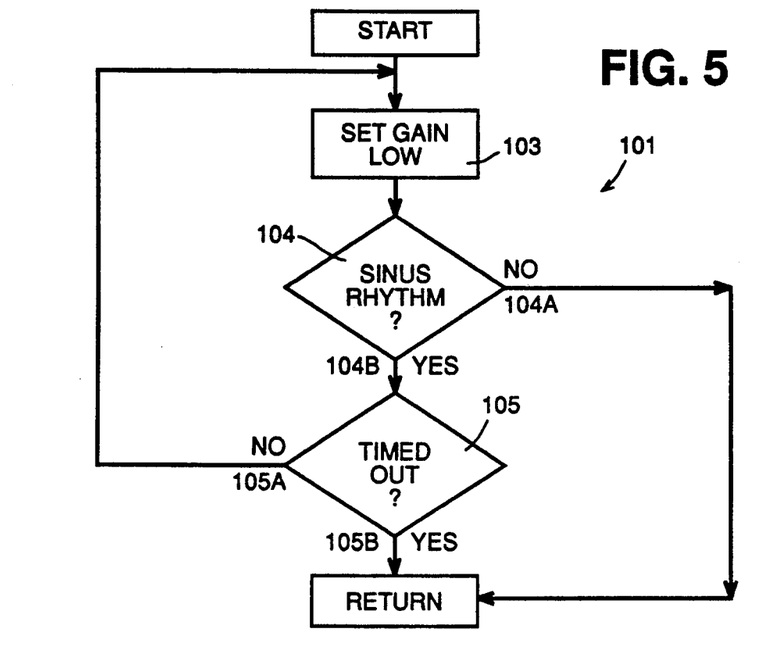
FIG. 5 is a logic flow chart of the low gain subroutine of FIG. 4.

Referring to FIG. 5, the neural network 21 makes fast and accurate decisions regarding sinus rhythm at 104 in conjunction with a timer at 105. In order to distinguish between sinus rhythm and a current of injury T-wave, it is necessary to temporarily adjust the detector circuit 37A (FIG. 2) to a low sensitivity level. This is accomplished by the low sensitivity subroutine 101. After the subroutine is accessed and started, the gain is temporarily set low at 103. This low sensitivity setting is lower than the medium sensitivity setting, which in turn, is lower than the high sensitivity setting. Immediately after the gain is set to the low level, a determination is made as to whether there is sinus rhythm at 104. If there is no sinus rhythm, the subroutine branches from 104A to RETURN and control is returned to the main program. However, if sinus rhythm is detected (104B), a determination is made at 105 as to whether a predetermined time interval since the delivery of tachyarrhythmia therapy has expired. This time interval may be programmed by the physician to account for the time required in the particular patient for the current of injury T-wave to be diminished to a level at which the detector will not trigger as if it is a QRS complex when the sensitivity is set to the medium level. If this time has elapsed (105B), the subroutine is terminated and control is returned to the main program. However, if this time has not elapsed, the subroutine loops from 105A back to 103 where the gain is again set at the low level. As long as sinus rhythm is detected and timeout has not occurred, the gain remains low. However, after the timeout occurs the subroutine is terminated and control is transferred back to the program of FIG. 4.

Figure 6:
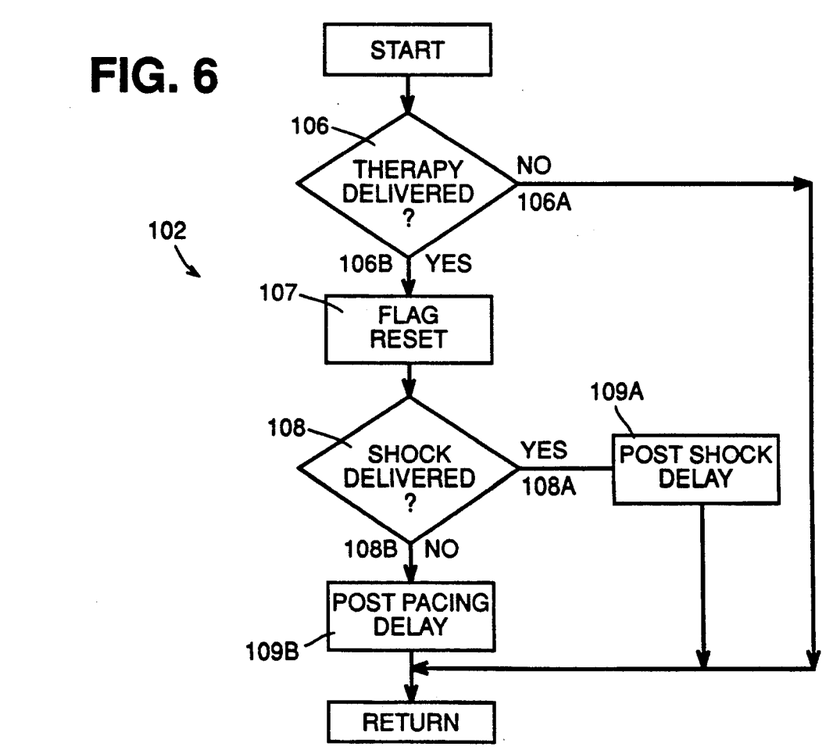
FIG. 6 is a logic flow diagram of the post therapy delay subroutine of FIG. 4.

Referring to FIG. 6, where the post therapy delay subroutine 102 is described, the neural network 21 again makes fast and accurate decisions regarding the delivery of therapy at 106 and the delivery of shock at 108. Since subroutine 102 is located in the return loop to step 91 for both reversion of a tachyarrhythmia at 97A and for lack of confirmation of a tachyarrhythmia at 99B (FIG. 4), it is necessary that there exist a mode wherein no delay is introduced. Specifically, if a tachyarrhythmia is detected at 93 but there is no confirmation at 95 and apparent asystole at 97 and no confirmation at 99 (even though the sensitivity has been set to the highest level at 98) then a tachyarrhythmia has led directly to asystole. In this case, since no therapy was administered, a delay in pacing is undesirable. Therefore when tachyarrhythmia therapy of any kind is delivered, a flag (not shown in FIG. 4) is set. This flag is read at step 106 to determine whether therapy has been delivered. If the answer is NO (106A) then control is immediately returned to the program of FIG. 4 and no delay is introduced. However, if the flag indicates that therapy has been administered, branching to 106B occurs. The flag is reset at 107. At 108 a determination is made as to whether a shock or pacing was last delivered. If the answer to the inquiry at 108 is YES then the program branches at 108A to a post shock delay 109A. After this delay, control is returned to the program of FIG. 4. The length of the post shock delay at 109A is programmable and is typically set so that the time between termination of tachyarrhythmia therapy at 96 and the delivery of bradycardia pacing at 92 is approximately 4.0 seconds. The actual delay introduced at 109A is less than 4 seconds as there is a small period of time generated by low gain subroutine 102 to determine whether sinus rhythm is present at 104 (FIG. 5) and bradycardia detection at 91 which typically has a programmed escape or standby interval of approximately 857 ms.

If a shock has not been delivered at 108 then antitachycardia pacing has occurred Subroutine 102 proceeds from 108B to 109B where a post pacing delay is introduced. The length of the post pacing delay is programmable but is generally selected so that the total delay from delivery of tachyarrhythmia pacing at 96 to the delivery of bradycardia pacing at 92 is in the order of 3.0 seconds. Specifically, the post pacing delay introduced at 109B is typically lower than 3.0 seconds. As is the case for the delay introduced at 109A, the remainder of the delay is made up by the time required to recognize the absence of sinus rhythm at 104 and the escape or standby interval of bradycardia detection at 91.

It will be understood that if sinus rhythm is detected at 104 (FIG. 5) the small additional delay introduced at 109A or 109B will be of little consequence. In this case, if a normal sinus rhythm has been restored, bradycardia will not be detected at 91 and pacing is not delivered in any event. However, should a bradycardia condition commence after the establishment of normal sinus rhythm by the delivery of tachyarrhythmia therapy, the small additional delay will not be critical. If it is desirable to avoid even this delay, the flag set when tachyarrhythmia therapy is delivered at 96 can be reset if normal sinus rhythm is detected at 104.

Figure 7:
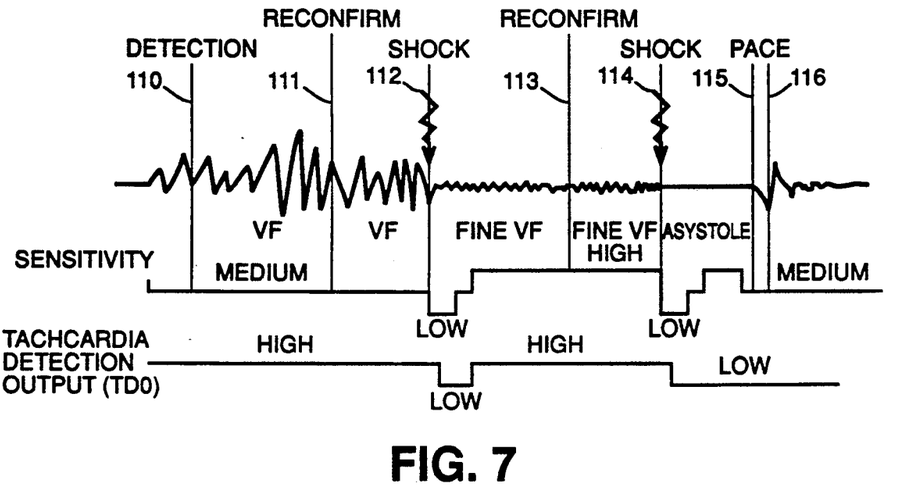
FIG. 7 is an ECG trace which illustrates the response of the device to various cardiac conditions when programmed to multiple sensitivity sensing.

Referring to FIG. 7, the ECG trace shows a VF detected at 110, the sensitivity is set at medium and the TDO (tachycardia detection output) provided by the algorithms used in microprocessor 16 is high showing a positive response from the medium sensitivity signal.

At 111, there is a reconfirmation of the VF. The reconfirmation is positive (the TDO still shows a high reading) and therefore the sensitivity setting is sufficient and it remains at the medium level.

At 112, a defibrillation shock is given. Immediately after the shock at 112, low sensitivity subroutine 101 is accessed and the TDO shows a low reading. The sensitivity is then switched from low sensitivity to medium sensitivity (FIG. 4, at 94) and then from medium sensitivity to high sensitivity (FIG. 4, at 98). The high sensitivity then shows a high TDO reading indicating detection of the presence of a fine (low amplitude) VF which was not detected at the low or medium sensitivity levels.

Reconfirmation is conducted at 113 (FIG. 4, at 99) showing the continued presence of the fine VF, as there is still a high reading on the TDO. Therefore at this stage the high sensitivity level remains in force.

At 114, defibrillation shock therapy is given. Immediately after the shock at 114, the low sensitivity subroutine 101B is again executed. Since sinus rhythm is not detected, the sensitivity returns to the medium level (FIG. 4, at 94) and then to the high level (FIG. 4, at 98) to pick up any fine VF which may be present. Post shock, the low TDO signal shows the absence or reversion of the VF and the presence of asystole, rather than VF, as no waveform is detected at the high sensitivity level. Since the TDO is low at the high sensitivity level, asystole is therefore assumed to be present. VVI pacing treatment is then given at 115.

At 116, sinus rhythm is detected as a result of the pacing therapy, with the sensitivity is switched to the medium sensitivity level. It is not necessary to use low sensitivity to distinguish between R-waves and current of injury T-waves in this late occurring sinus rhythm complex.

Figure 8:
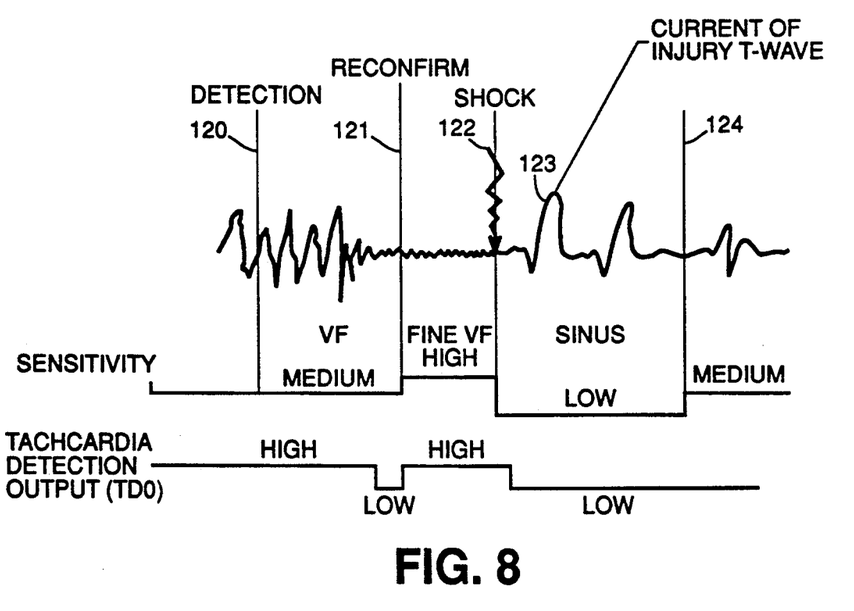
FIG. 8 is another ECG trace which illustrates the response of the device to various cardiac conditions when programmed to multiple sensitivity sensing.

Referring to FIG. 8, a VF is detected at 120, the sensitivity signal is set to medium sensitivity at 94 and a high TDO reading shows that VF is present and that the medium sensitivity setting is sufficient at this stage.

The VF is still present at 121 but has developed into a lower amplitude or fine VF at 125. When this amplitude reduction occurs, the signal is "sub-threshold" relative to the medium sensitivity signal. As a result, the TDO switches from high to low. At the reconfirmation point 121, the presence of the low TDO signal triggers a switchover from medium sensitivity level to high sensitivity level. The high sensitivity level picks up the lower amplitude fine VF and a high TDO reading is again generated.

Defibrillation shock therapy is given at 122. Low sensitivity subroutine 101 is accessed immediately post shock. The TDO signal goes low post shock showing the absence of VF, and sinus rhythm is detected at 123. Subroutine 101 then maintains, for the programmed timeout interval at 105, low sensitivity to distinguish R-waves from high amplitude current of injury T-waves.

If the medium sensitivity level were selected at 123, then double sensing of the R and T-waves would occur, causing an incorrect reading along with correspondingly incorrect therapy which would cause severe problems and great discomfort to a patient. At 124, when the timeout for low sensitivity has elapsed (FIG. 5, at 105) there is a switchover from low sensitivity to medium sensitivity to pick up the R-waves of the normal sinus rhythm complex. If the duration of the timeout has been properly programmed, by this time the high amplitude current of injury T-wave has gradually decreased in amplitude to a normal amplitude T-wave.

The sensitivity levels in the device which are not variable but are held at fixed, discrete levels during normal operation are programmable by a physician. During programming or patient evaluation, an external programmer (not shown), which communicates with telemetry circuit 38, may be used for switching interchangeably from any one sensitivity level to any other sensitivity level.

Figure 9A:
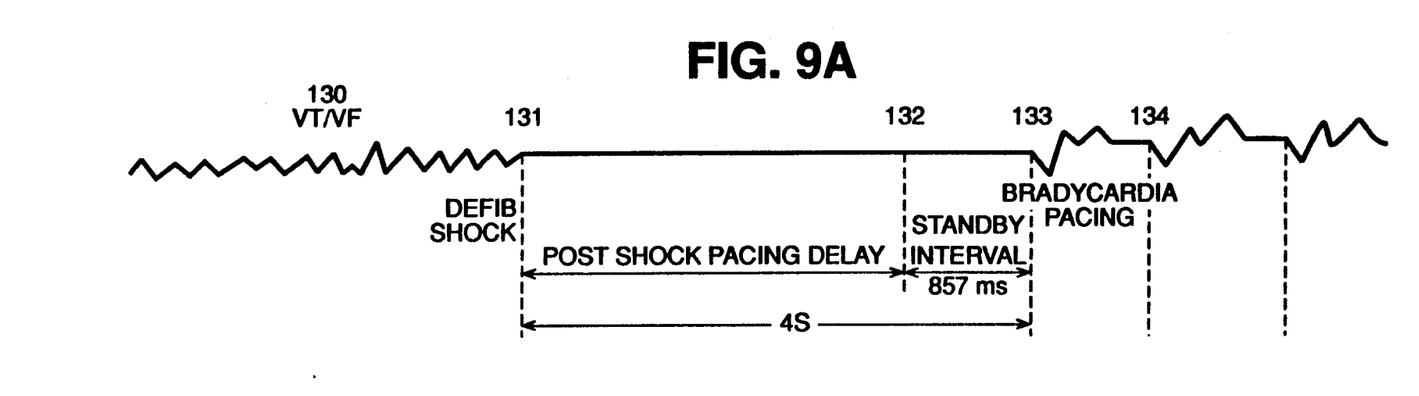
FIG. 9A is an ECG trace which illustrates bradycardia pacing after defibrillation shock with post shock delay.

Referring to FIG. 9A, there is depicted an ECG trace outlining a bradycardia pacing sequence after defibrillation shock with a post shock pacing delay. At 130, a VT/VF arrhythmia has developed. Defibrillation shock therapy is applied at 131. As shown, the defibrillation shock, which has succeeded in reverting the VT/VF arrhythmia, is followed by a post shock pacing delay interval extending between 131 and 132. At 133, asystole is detected and bradycardia pacing is commenced approximately 4 seconds after the delivery of the defibrillation shock and continues at 134. The pro-arrhythmic effect of a premature recommencement of bradycardia support pacing immediately post reversion is avoided, as there is sufficient time for the conduction system of the patient's heart to be reorganized and susceptible to bradycardia support pacing.

Figure 9B:
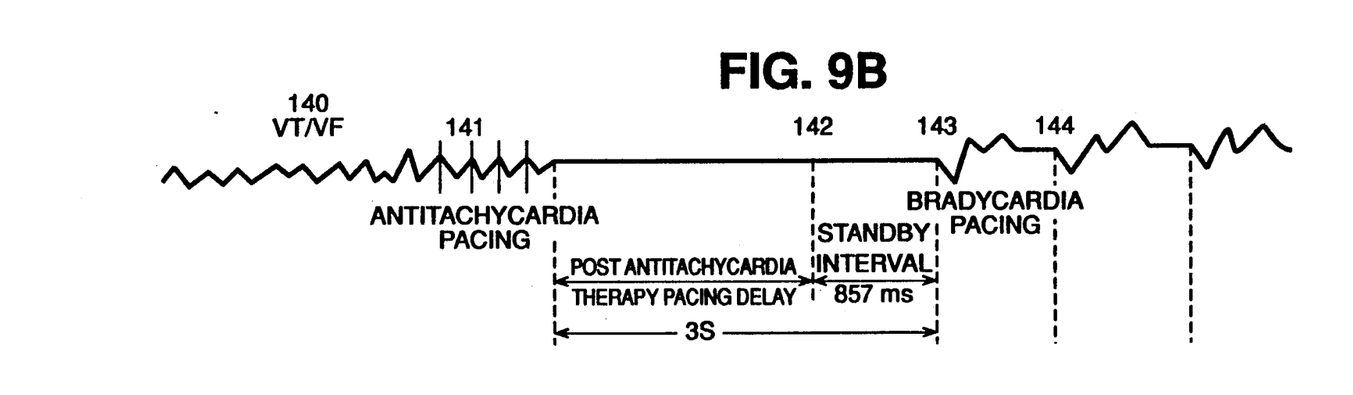
FIG. 9B is an ECG trace which illustrates bradycardia pacing after antitachycardia pacing with post antitachycardia pacing delay.

Referring to FIG. 9B, there is depicted an ECG trace outlining a bradycardia pacing sequence after antitachycardia pacing with a post antitachycardia pacing delay. At 140, a VT/VF arrhythmia has developed. Antitachycardia pacing therapy is applied at 141. As shown, the antitachycardia pacing therapy, which has succeeded in reverting the VT/VF arrhythmia, is followed by a post antitachycardia pacing delay interval extending between 141 and 142. At 143, asystole is detected and bradycardia pacing is commenced approximately 3 seconds after the delivery of the antitachycardia pacing therapy and continues at 144. Again, the pro-arrhythmic effect of a premature recommencement of bradycardia support pacing immediately post reversion is avoided, as there is sufficient time for the conduction system of the patient's heart to be reorganized and susceptible to bradycardia support pacing.

Figure 10:
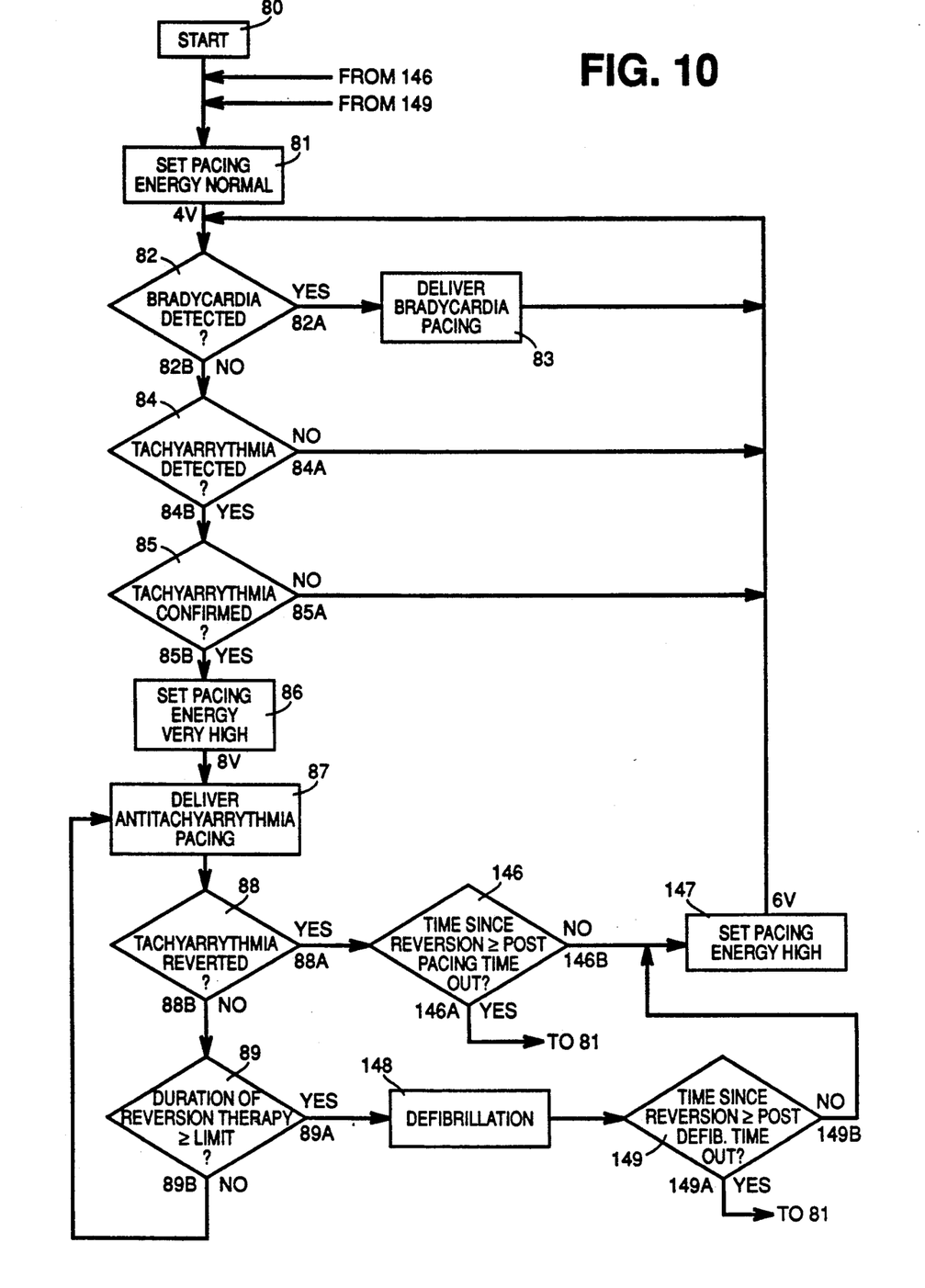
FIG. 10 is a logic diagram which illustrates the neural network flow control for therapy involving changes in pacing energy.

FIG. 10 is a logic diagram of the neural network flow control for changing pacing energies. The logic flow control utilizes the neural network 21 for fast and accurate decision making. Decisions are necessary at 82 (bradycardia detection), 84 (tachyarrhythmia detection), 88 (tachyarrhythmia reversion), 89 (duration of reversion therapy), and 149 (time since reversion compared to post defibrillation timeout). The start of the flow control is shown at 80, and at 81 the pacing energy is set to the normal value corresponding to 4 volts. At 82 a determination is made as to whether a bradycardia condition exists. If it does, then bradycardia pacing is delivered at normal pacing energy at 83.

If there is no bradycardia condition as shown at 82B, then branching occurs based on whether or not there is a tachyarrhythmia condition, as shown at 84. If there is no detection of a tachyarrhythmia condition as shown at 84A, then the program loops back through 82. If a tachyarrhythmia condition is detected at 84 as shown at 84B, then a confirmation of the tachyarrhythmia is given at 85. If a tachyarrhythmia condition is not confirmed as shown at 85A, then the program loops back to 82. If a tachyarrhythmia condition is confirmed, as shown at 85B, the pacing energy is set to the very high level corresponding to 8 volts as shown at 86. Antitachyarrhythmia therapy is then delivered to the patient as shown at 87. A determination is made at 88 as to whether or not the tachyarrhythmia has been reverted. If the tachyarrhythmia condition has not been reverted, as shown at 88B, then further antitachyarrhythmia therapy is delivered at 87. The therapy continues until reversion takes place at 88A, or for a given limited time as determined at 89 and as more fully explained below.

Reversion of a tachyarrhythmia at 88A starts a post-pacing timer at 146. As long as the time elapsed from reversion does not exceed a predetermined time interval, the pacing energy is set to the high level (corresponding to 6 volts) at 147 and it will remain at that high level until the expiration of the post-pacing timeout period at 146. The post-pacing timeout is a programmed period of time following antitachyarrhythmia therapy (in this case pacing) where the pulse energy is set at the high level in order to prevent a loss of capture due to the high probability of the heart being in a traumatic state. Programming may be performed by the physician either just prior to implantation, or changed after implantation through telemetry circuit 38 (FIG. 2).

If the pacing energy is high and the post-pacing timeout period is exceeded as shown at 146A, the command is given to set the pacing energy to the normal value corresponding to 4 volts at 81. If the time since tachyarrhythmia reversion has not exceeded the post-pacing timeout period, or if the pacing energy has been set (at 81) to the normal 4 volt value following the expiration of the post-pacing timeout period as shown at 146A, then at 82 branching occurs based on whether or not bradycardia has been detected. If a bradycardia condition is detected as shown at 82A, then bradycardia pacing is delivered as shown at 83. The pacing pulse energy will be either at the level corresponding to 6 volts (high) if the post-pacing timeout period has not expired, or at the level corresponding to 4 volts if the post-pacing timeout period has expired.

In any event, following reversion of the tachyarrhythmia condition, if post-pacing timeout has not occurred, at 146B the pacing energy is set to the high level of 6 volts, as shown at 147, and the loop passes back to 82. If the post-pacing timeout has occurred, at 146A branching to 81 occurs and the pacing energy is set to normal.

If there has been no indication of reversion at 88 and the time limit set at 89 for the duration of reversion therapy is exceeded, branching occurs to 89A and defibrillation is applied at 148. A post-defibrillation duration timer at 149 is reset, and the pacing energy is then set to the high level corresponding to 6 volts at 147. The program then loops back to 82. If the post-therapy (in this case, post-defibrillation) timeout has occurred, at 149A branching to 81 occurs and the pacing energy is set to normal.

In FIG. 10, the timeouts for the high energy pacing may be different time intervals as programmed into or fixed by the timers 146 and 149 depending upon whether antitachycardia has been reverted at 88 or defibrillation has occurred at 148. It is possible to implement a system wherein the same programmable timer is used in both cases by, for example, eliminating timer 149 and connecting the output of block 148 as an additional input to timer 146 which could then be called, generally, a post-therapy timer. In that case it is also desirable that bradycardia support pacing be inhibited for programmable periods of time after antitachycardia pacing or defibrillation which reverts a tachyarrhythmia to avoid any pro-arrhythmic effect. The use of such a delay is described in above-mentioned U.S. Pat. No. 4,940,054.

It will be recognized that timers 146 and 149 of FIG. 10 correspond in function and operation to those of post pacing delay 109B and post shock delay 109A, respectively (FIG. 6).

As noted above, physiological signals other than an unprocessed or processed ECG signal may be used as input signals for the operation of the present invention. In this regard, reference is made to the above-mentioned copending application Ser. No. 481,364 of Kenneth A. Collins. Other physiological signals mentioned herein may be acquired by means well known in the art.

Preferably, the neural network is used to control detection, diagnosis and therapy, while the microprocessor is used to perform basic control and housekeeping functions. However, it will be recognized by those skilled in the art that in alternative embodiments, these responsibilities may be shared by the microprocessor and the neural network or may overlap so as to provide a measure of redundancy.

Although the invention has been described with respect to particular embodiments, it is to be understood that these embodiments are merely illustrative of the application of the principles of the invention. Numerous modifications may be made therein and other arrangements may be devised without departing from the spirit and scope of the invention.

What is claimed is:

1. An arrhythmia control apparatus, comprising:
   means for acquiring physiological signals representative of heart activity of the patient;
   means for processing said physiological signals, said processing means including a plurality of neural networks coupled to said acquiring means for receiving the physiological signals, classifying said signals into pathological and non-pathological categories, and selecting therapy to be applied to the heart if a pathological condition is determined to be present in the heart, said plurality of neural networks being arranged in series so that the output of one of said networks comprises the input of another of said networks, one of said networks selecting the therapy to be delivered to the heart in the event a pathological condition is determined to be present in the heart; and,
   therapy means coupled to said processing means for delivering to the heart the therapy selected by said processing means.

2. An arrhythmia control apparatus according to claim 1, wherein one of said networks extracts a series of features from said physiological signals.

3. An arrhythmia control apparatus according to claim 1, wherein one of said networks classifies said physiological signals into said pathological and non-pathological categories.

4. An arrhythmia control apparatus comprising:
   means for acquiring physiological signals representative of hearty activity of the patient;
   means for processing said physiological signals, said processing means including a plurality of neural networks coupled to said acquiring means for receiving the physiological signals, classifying said signals into pathological and non-pathological categories, and selecting therapy to be applied to the heart fi a pathological condition is determined to be present in the heart, said plurality of neural networks being arranged in series so that the output of one of said networks comprises the input of another of said networks, a first one of said plurality of neural networks extracting a series of features from said physiological signals, a second one of said plurality of neural networks being serially connected to said first neural network to receive said extracted features and classify said physiological signals into pathological and non-pathological categories based on said features, and a third one of said plurality of neural networks being serially connected to said second neural network and, in the event a pathological condition is determined to be present by said second network, selecting a therapy to be delivered to the heart based on such pathological condition; and, therapy means coupled to said processing means for delivering to the heart the therapy selected by said processing means.

5. An arrhythmia control apparatus according to claim 1, wherein said apparatus further includes a power supply, sensing means for detecting QRS events of the heart, and a microprocessor coupled to said power supply, said sensing means and said plurality of neural networks for controlling power to said plurality of neural networks, said microprocessor controlling the flow of power to said neural networks such that power is supplied to less than all of said neural networks in the absence of a pathological condition of the heart and to all of said neural networks when a pathological condition is determined to be present in the heart.

6. A method of controlling arrhythmias in a patient's heart, comprising the steps of:

acquiring physiological signals representative of heart activity of the patient;

providing a processing means, including a plurality of neural networks, for receiving said physiological signals;

operating said neural networks in such a manner that the output of one of said networks comprises the input of another of said networks;

providing therapy means for delivering one of a plurality of different therapies to the heart;

inputting said physiological signals into one of said neural networks;

processing said physiological signals in said neural networks to detect whether an arrhythmia is present in the patient's heart and to select a therapy to be applied to the heart if said processing means determines an arrhythmia to be present;

selecting, in one of said neural networks, the therapy to be delivered to the heart in the event a pathological condition is determined to be present in the heart; and delivering to the heart the therapy selected by said processing means.

7. A method of controlling arrhythmia according to claim 6, further comprising extracting a series of features from individual senses physiological waveforms in one of said neural networks.

8. A method of controlling arrhythmias in a patient's heart, comprising the steps of:

acquiring physiological signals representative of heart activity of the patient;

providing a processing means, including a plurality of neural networks, for receiving said physiological signals;

operating said neural networks in such a manner that the output of one of said networks comprises the input of another of said networks;

providing therapy means for delivering one of a plurality of different therapies to the heart;

inputting said physiological signals into one of said neural networks;

processing said physiological signals in said neural networks to detect whether an arrhythmia is present in the patient's heart and to select a therapy to be applied to the heart if said processing means determines an arrhythmia to be present;

said processing step including the sub-steps of extracting a series of features from said physiological signals in a first one of said neural networks, receiving said extracted features and classifying said physiological signals into pathological and non-pathological categories based on said features in a second one of said neural networks, and in the event a pathological condition is determined to be present by said second neural network, selecting a therapy to be delivered to the heart based on such pathological condition; and, delivering to the heart the therapy selected by said processing means.

9. A method of controlling arrhythmia according to claim 8, further comprising the steps of providing a power supply, sensing means for detecting QRS events of the heart, and a microprocessor coupled to the power supply, the sensing means and the plurality of neural networks for controlling power to the plurality of neural networks, and controlling the flow of power to said neural networks by said microprocessor in such a way that power is supplied to less than all of said neural networks in the absence of a pathological condition of the heart and to all of said neural networks when a pathological condition is determined to be present in the heart.

10. A method of controlling arrhythmia according to claim 8, further comprising the step of programming selected parameters utilized by said processing means in detecting arrhythmias.

* * * * *